United States Patent [19]

Welebir

[11] 4,455,162

[45] * Jun. 19, 1984

[54] 1-TRIACONTANOL PLANT GROWTH STIMULATOR FORMULATIONS

[75] Inventor: Andrew J. Welebir, Arlington, Va.

[73] Assignee: Biochemical Research Corporation, Falls Church, Va.

[*] Notice: The portion of the term of this patent subsequent to Jun. 8, 1999 has been disclaimed.

[21] Appl. No.: 324,416

[22] Filed: Nov. 24, 1981

Related U.S. Application Data

[63] Continuation-in-part of Ser. No. 202,705, Oct. 30, 1980, Pat. No. 4,411,685, which is a continuation-in-part of Ser. No. 146,005, May 2, 1980, Pat. No. 4,333,758, which is a continuation-in-part of Ser. No. 047,696, Jun. 12, 1979, abandoned.

[51] Int. Cl.³ .............................................. A01N 59/00
[52] U.S. Cl. ............................................. 71/80; 71/65; 71/122
[58] Field of Search ....................... 71/65, 122, 80, 83

[56] References Cited

U.S. PATENT DOCUMENTS

| | | | |
|---|---|---|---|
| 1,703,362 | 2/1929 | Popoff | 71/65 |
| 2,558,762 | 7/1951 | Kohr, Jr. et al. | 71/65 |
| 3,630,717 | 12/1971 | Miller | 71/122 |
| 3,756,801 | 9/1973 | Herschler | 71/65 |
| 4,150,970 | 4/1979 | Ries et al. | 71/122 |
| 4,169,716 | 10/1979 | Ashmead | 71/122 |
| 4,169,717 | 10/1979 | Ashmead | 71/77 |
| 4,230,485 | 10/1980 | Ohlrogge | 71/122 |
| 4,333,758 | 6/1982 | Welebir | 71/89 |

OTHER PUBLICATIONS

Pooviah et al., Plant Physiol. 58, pp. 783–785 (1976).
Pooviah et al., Plant Physiol. 54 pp. 289–293 (1974).
Leopold, Plant Growth Regulators pp. 33–41 (1979).
Leopold et al., Plant Growth Substances pp. 780–788 (1974).

*Primary Examiner*—Glennon H. Hollrah
*Attorney, Agent, or Firm*—Birch, Stewart, Kolasch & Birch

[57] ABSTRACT

A plant growth stimulator formulation including a substantially water-soluble concentrate solution of 1-triacontanol, a polar organic solvent, and metal ions having a valence of +2 or more. Metal ions disclosed in the present invention markedly increase the growth-stimulating effect of 1-triacontanol when applied to plant life resulting in crop yield increases which may be as high as 50 to 100% over controls. The formulations are effective on all plant life tested, including field corn, soybeans, wheat and grains, vegetables, and other plant life. In addition, additive effects are noted in successive generations of plant life to which the formulations are applied.

30 Claims, 4 Drawing Figures

Formulation 1 = ○    Formulation 2 = ●

Formulation 1 = ○    Formulation 2 = ●

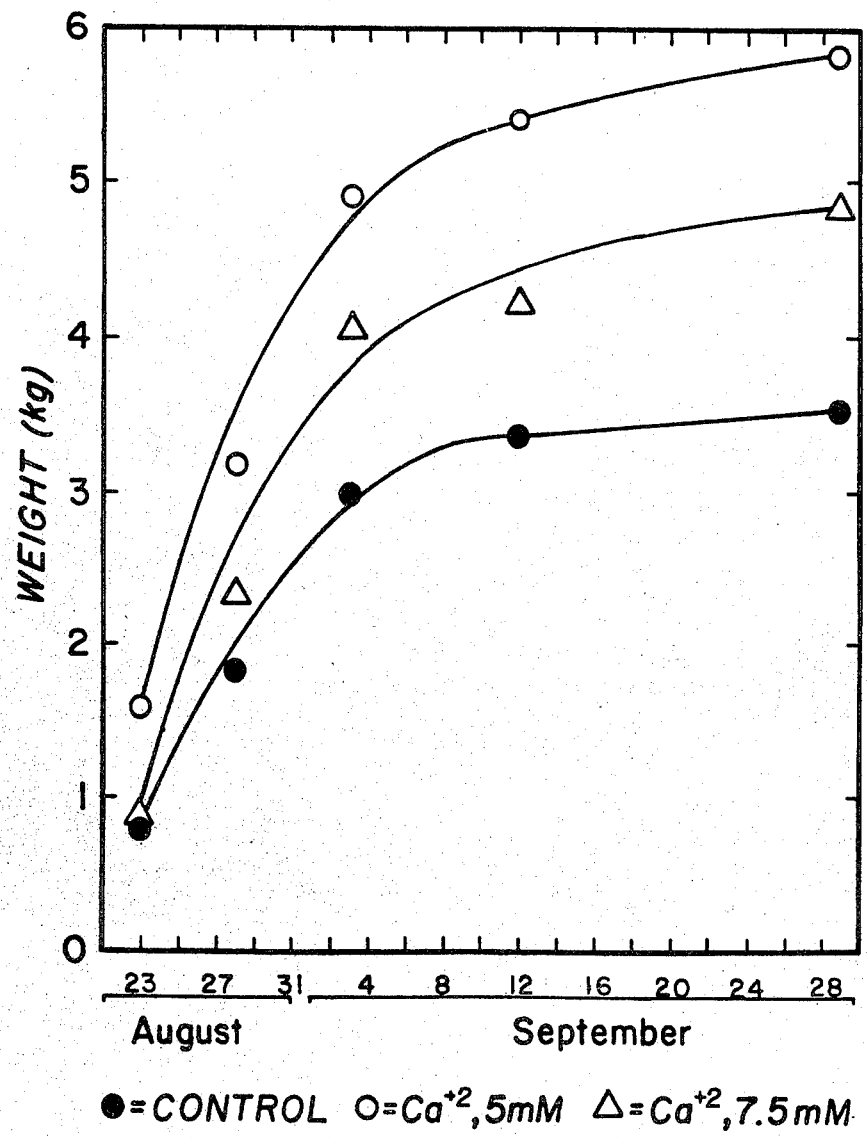

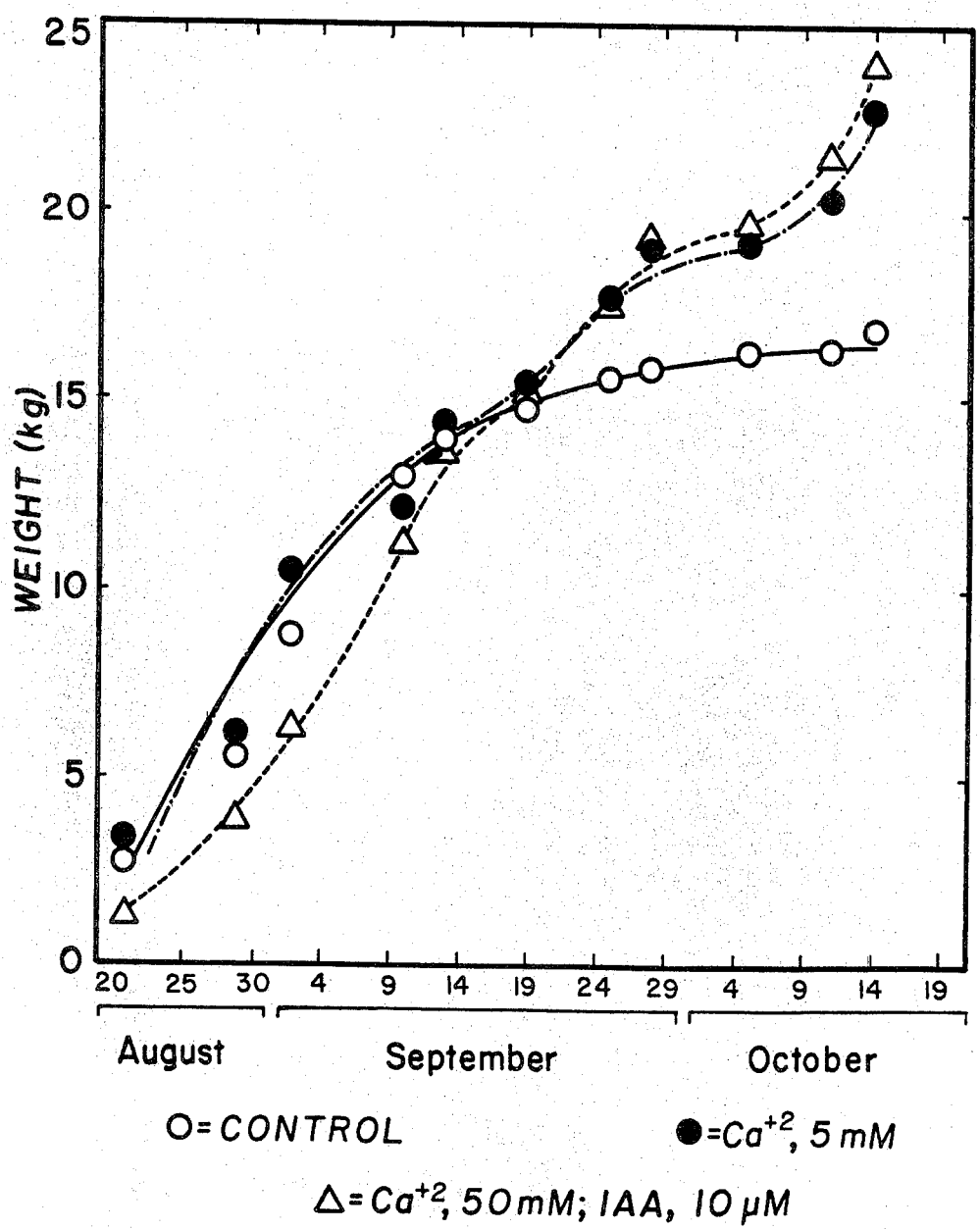

1-TRIACONTANOL PLANT GROWTH STIMULATOR FORMULATIONS

This application is a continuation-in-part (CIP) of copending U.S. application Ser. No. 202,705 filed Oct. 30, 1980, now U.S. Pat. No. 4,411,685 which is a CIP of U.S. Ser. No. 146,005 filed May 2, 1980, which issued as U.S. Pat. No. 4,333,758 on June 8, 1982, which is a CIP of U.S. Ser. No. 47,696 filed June 12, 1979, now abandoned.

BACKGROUND OF THE INVENTION

1. Field of the Invention

The present invention relates to a chemical composition which, when applied to growing plants, is effective in stimulating plant growth. More particularly, the present invention relates to a chemical formulation of 1-triacontanol in combination with a polar organic solvent, metal ions, and water.

2. Description of the Prior Art

Recently, 1-triacontanol, $CH_3(CH_2)_{28}CH_2OH$, has been under investigation as a naturally-occurring plant growth stimulant (see Ries, et al., Science, 195:1339 (1977)). In fact, field trials and greenhouse trials are presently being conducted in order to optimize the conditions under which 1-triacontanol formulations can be effectively applied to plant life in order to obtain consistent increases in growth and crop yields.

In the research that is presently being conducted widely, utilizing 1-triacontanol as a plant growth stimulant, use is being made of relatively large quantities of surfactants in the chemical formulations in an attempt to disperse the 1-triacontanol effectively in water. Of course, the use of large amounts of water is essential in order to economically and effectively apply the chemical formulation to large areas of growing plants. Accordingly, it is imperative to render the 1-triacontanol water-soluble so that it may properly be applied using large amounts of water to plant life. However, the organic solvents which are presently being utilized to aid in emulsification of 1-triacontanol in water, for example, the use of chloroform or other water-insoluble solvents, along with surfactant additives, tend to be detrimental to plant life and to the environment. Thus, surfactants can hinder the entry of triacontanol into plants, rendering the effects of the compound ineffective.

During the course of research leading to the present invention, it has been discovered, surprisingly, that auxins and other plant growth substances alter the effects of 1-triacontanol. More specifically, the naturally-occurring auxin, indole-3-acetic acid (IAA) has been found to counteract any growth-promoting effect of 1-triacontanol. Auxins and 1-triacontanol are normally considered plant growth stimulating agents, and the investigation into the inhibitory interaction between the two substances led to the discovery that metal ions having a positive valence of +2 or more not only reverse the inhibition, but have an unexpected synergistic effect on the growth-stimulating effect of 1-triacontanol. Furthermore, this effect occurs in the presence of free metal ions which are not complexed or chelated. For example, the addition of surfactants such as Tweens, which effectively complex the metal ions, show either a decrease in plant growth when combined with 1-triacontanol formulations containing metal ions or show no effect at all. This same effect may be observed using the formulations disclosed in the U.S. Pat. No. 4,169,716 by Ashmead which teaches that 1-triacontanol may show a synergistic effect when combined with certain metal proteinates and a variety of other plant growth substances. These complexed proteinates (metal ions chelated with amino acids and peptides), therefore, are not considered to be within the scope of the present invention. Also, these complexes, together with those disclosed in U.S. Pat. No. 4,169,717 by Ashmead, appear to show a much lesser effect than the formulations of the present invention, and are employed under hydroponic conditions which may include surfactant additives in the case where 1-triacontanol is added. U.S. Pat. No. 4,169,716, which employs 1-triacontanol in the case of hydroponically grown wheat, furthermore, does not utilize free metal ions, and, in fact, both of the above mentioned U.S. Patents advise against the use of said metal ions due to the plant's inability to absorb same. The best mode of the present invention involves foliar application of the formulations containing free metal ions.

Calcium and other metal ions having a valence of +2 or more are known to alter the effects of the five classes of plant hormones. These include auxins (indole-3-acetic acid (IAA), 2,4-dichlorophenoxyacetic acid (2,4-D), 2,4,5-trichlorophenoxyacetic acid (2,4,5-T), naphthalene acetic acid (NAA), indole-3-acetonitrile, indole-3-butyric acid, naphthalene acetamide, 2-methyl-1-naphthalene acetic acid, 2-methyl-1-naphthalene acetamide, 2,4-dichlorobenzoic acid, and other compounds or analogs which promote cell elongation and have an affinity for auxin receptors), gibberellins (gibberellic acid ($GA_3$) or other gibberellins), cytokinins (such as kinetin (6-furfurylamino purine), dimethylallylaminopurine, methylamino purine, methylhydroxymethylallylamino purine, phenylpurine, benzylurine, N-ethylpurine, N-propylpurine, diphenylurea, etc.), ethylene, and abscisic (see Poovaiah and Leopold, Plant Physiol., 58:783 (1976)). The following cations have the ability to increase auxin binding to cell membranes and inhibit auxin-stimulated growth in the order:

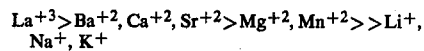

(Poovaiah and Leopold, Plant Physiol., 58:182 (1976)). These metal ions are contained in the well-known Hofmeister series.

Indole-3-acetic acid (IAA), the endogenous auxin which occurs widely in all plants, is known to rapidly stimulate cell elongation and enlargement, a process that involves loosening of the cell wall. IAA occurs primarily in esterified form, the myo-inositol ester comprising about fifty percent in corn (Zea mays). Only about one to ten percent of the relatively large amount of IAA in corn occurs as free IAA. Auxin binding to cell membranes is a reversible process with a $K_m$ between $10^{-6}$ and $5 \times 10^{-5}$M. There are apparently two binding sites for auxins. Site 1 binds both active and inactive auxin analogs while site 2 appear to be auxin specific. A wide variety of synthetic auxins (not naturally-occurring) show enhanced activity over the naturally-occurring auxin, IAA (for example NAA, 2,4-D, 2,4,5-T, etc.).

While the metal ions of the Hofmeister series having a valence of +2 or more are known to effect auxin binding and are very effective in producing a synergistic effect when combined with 1-triacontanol using the methods of the present invention, other metal ions such as zinc, lead, cadmium, etc. are effective and in some cases superior to the Hofmeister series metal ions. Since these other metal ions are useful and are not known to affect auxin binding, the synergistic effect observed in combination with 1-triacontanol may not be related to increased auxin binding. Furthermore, since the pH of the formulations of the present invention must be maintained over 7, auxin binding would necessarily be inhibited rather than promoted (see Plant Physiol., 59:357 1977)). Therefore, no explanation for the surprising synergistic effect of metal ions having a valence of +2 or more in the 1-triacontanol formulations is apparent.

Since surfactant additives or other additives which effectively complex the metal ions of the present invention may not be used in carrying out the best mode of the invention, research by the present inventor has led to the discovery that the incorporation of a polar organic solvent must be used. The polar organic solvent should be one in which 1-triacontanol is soluble to some extent, and also one that shows a solubility in water. Such solvents are disclosed in U.S. Ser. No. 47,696, filed June 12, 1979, and U.S. Ser. No. 146,005, filed May 2, 1980, both by the present inventor. The polar solvents of the present invention include, but are in no way limited to, water soluble ketones, alcohols, ethers, acids, amines, and dipolar aprotic solvents (such as dimethyl formamide, dimethyl sulfoxide (DMSO), and hexamethyl phosphoramide), and the like.

The use of such solvents does not conflict with uses in the prior art. For example, U.S. Pat. No. 4,150,970 by Ries, et al., mentions solvents in which 1-triacontanol is soluble, such as ethyl alcohol, however, the use of such solvents to form concentrated solutions to be diluted with relatively large amounts of water is not disclosed or implied. Also, the formulation used in the Patent by Ries, et al., namely a nonpolar solvent to form a concentrate which requires a surfactant to emulsify same, is shown by the present invention and related applications by the present inventor to be inferior to formulations containing a polar organic solvent. In the following description of the preferred mode of the invention it will become clear that the solutions containing a polar organic solvent show improved increases and reproducibility in plant growth stimulation when used in the 1-triacontanol formulations described therein.

U.S. Pat. No. 2,168,550, issued September, 1937 to Zimmerman, et al., discloses useful improvements in formulating auxins for use in promoting root growth. These include the use of alcohols (which are polar organic solvents) to aid in the solubility of the auxins. It should be noted that auxins are equally effective when formulated in a number of ways well known in the art, and the teachings of Zimmerman, et al., refer only to a convenient method of formulation of said auxins. The use of polar organic in the present invention, on the other hand, is required for the reproducibility of results and essential when the metal ions of the invention are incorporated into 1-triacontanol formulations to circumvent the necessity of having to add a metal-complexing surfactant additive to aid in emulsification when a nonpolar solvent is employed.

The disclosure by Ohlrogge in U.S. Pat. No. 4,230,485, issued Oct. 28, 1980, includes acetone (a polar organic solvent) to aid in the formulation of 1-triacontanol, however, this pertains only to the use of said formulation on field corn at a stage of application after tassel initiation. The disclosure is not within the scope of the present invention since it pertains to foliar application of a 1-triacontanol formulation at a stage of growth of field corn outside the scope of the present invention (preferably at the two to five leaf stage and before tassel initiation).

Other documents, such as U.S. Pat. No. 2,277,744 by Cupery, et al., Mar. 31, 1942, and U.S. Pat. No. 3,360,717 by Miller, Dec. 28, 1971, and a number of references covering the growth effects of metal ions on plant life and modes of application of various pesticides and plant growth substances show no reference to formulations of 1-triacontanol formulation or application, either with or without metal ion additives, are of no utility with regard to the present invention as a result of close inspection by the present inventor. The benefits and marked advantages over the prior art of the formulations of the present invention will become apparent in the following description.

SUMMARY OF THE INVENTION

Accordingly, it is an object of the present invention to provide an inexpensive and effective means of formulating triacontanol without the use of surfactant additives or organic solvents which pose a threat to plant life and/or the environment. Also, since it appears that the action of triacontanol requires the presence of a metal ion having a valence of +2 or more for reproducible activity on almost all plants, surfactants must be avoided in order to prevent complexation of the metal ions.

A second object of the present invention is to provide formulations of triacontanol containing polar organic solvents which aid in the dissolution of said triacontanol in relatively large volumes of water containing metal ions, resulting in a product which poses no threat to the environment and/or plant life, shows improved stability over formulations containing nonpolar organic solvents with surfactant additives, and is easily prepared.

A third object of the present invention is to provide methods whereby the disclosed formulations may effectively to applied to areas of growing plant life to increase the growth rate of said plant life.

A fourth object of the present invention is to provide a means of increasing the yields of crops in the field, a means of increasing the growth of other plants, such as trees and grasses, and a means of improving the quality and marketability of ornamental plants.

A fifth object of the invention is to provide a means whereby successive generations of plant life show increases in growth and crop yield, which may subsequently be increased additively with the additional application of the formulations.

A sixth object of the invention is to provide formulations of 1-triacontanol which are effective in reversing the effects of herbicidal agents and weed killers.

Pursuant to the present invention, the above problems have been eliminated, and significant improvements made, by providing a chemical formulation which can be used with water for application to plant life. According to the present invention, 1-triacontanol is first dissolved in a polar organic solvent in an amount sufficient to form a water-soluble concentrate. Typically, a concentrate can be formed by dissolving one part (grams) of 1-triacontanol in up to about 5,000,000 parts (milliliters) of polar organic solvent, preferably between 10,000 and 500,000 parts of solvent, more preferably between 10,000 and 160,000 parts of solvent, and most preferably between 17,000 and 80,000 parts of solvent. The polar organic solvent can be any water-soluble solvent or solvent mixture containing one or more functional groups, and which renders the 1-triacontanol solution soluble in water. The solution is then dissolved in a relatively large quantity of water with stirring and/or shaking prior to spraying. Alternately, other plant growth substances may be dissolved in the concentrate or the water solution, which contains the metal ions of the instant invention.

The polar organic solvents which are utilized in the present invention to aid in the solubility of 1-triacontanol include, but are not limited to, ketones, alcohols, water-soluble ethers, glycols, sulfoxides, organic carboxylic acids, amines, dipolar aprotic solvents, and the like. Typical polar organic solvents include acetone, methyl ethyl ketone, diethyl ketone, cyclohexanone, methanol, ethanol, propanol, isopropanol, butanol, isobutanol, ethylene glycol, propylene glycol, diethylene glycol, glyme, diglyme, dioxane, tetrahydrofuran, acetic acid, formic acid, propionic acid, lower aliphatic amines, dimethyl sulfoxide, dimethylformamide, and hexamethyl phosphoramide.

Typical ratios of the solutions of 1-triacontanol in the polar organic solvents may vary from 1:1 to 1:10,000 parts by volume, preferably 1:50 to 1:4,000 parts by volume, depending upon the desired concentration of the 1-triacontanol in the final solution.

In accordance with another aspect of the present invention, it has been discovered that indole-3-acetic acid (IAA), which normally stimulates cell elongation and plant growth, effectively inhibits the growth-stimulating effects of 1-triacontanol in plants when the two are applied to seedlings as a foliar spray simultaneously. Other plant growth substances were added to the 1-triacontanol formulations in order to the study the effects of the plant growth substances on the effects of 1-triacontanol in an attempt to improve the growth response of the 1-triacontanol formulations. The following plant growth substances were tested: IAA, gibberellic acid ($GA_3$), kinetin (a cytokinin), 2,4-D (2,4-dichlorophenoxyacetic acid), 2,3,5-triiodobenzoic acid (TIBA), and naphthalene acetic acid (NAA). Various salts were also tested for their effectiveness in improving the plant growth-stimulating properties of the 1-triacontanol formulations. The salts tested included $CaCl_2$, $LaCl_3$, $Ce(SO_4)_2$, $MgCl_3$, $PbCl_2$, $SrCl_2$, $ZnCl_2$, $MnCl_2$ $BaCl_2$, $CoCl_2$, and $CuCl_2$. These salts are, in part, members of the membrane-destabilizing salts contained in the Hofmeister series, and are known to inhibit auxin-induced growth through increased binding to cell membranes, as previously described. Other salts are not contained in this series, however, but are found to be equally effective in producing a synergistic effect in the 1-triacontanol formulations, in spite of the fact that they are not known to inhibit auxin-induced growth. While, in most cases, all the salts were employed as the chloride salts, no effect is attributed to the counter ion, since differential effects are observed with different chloride salts. Furthermore, this fact is acknowledged in the prior art where metal ions have been studied with each of the five plant hormones (auxins, gibberellins, cytokinins, abscisic acid, and ethylene). While some of the metal ions described above effect the responses to the plant hormones, these include only those ions contained in the Hofmeister series, especially $Ca^{+2}$ and $La^{+3}$. 1-Triacontanol, furthermore, is not an established plant hormone, and structurally cannot compete for the receptor sites of these plant hormones (a plant hormone is a chemical compound which is synthesized at one site within the plant and transferred to a different site where growth activity is influenced in a specific way).

It has been found that the metal ions of the present invention are most effective when applied to the leaves of growing plants (i.e., by foliar application) by spraying the formulations at concentrations which may range from 1 molar to about 10 µM, preferably at concentrations of between about 100 mM to 0.1 mM, and more preferably at concentrations between about 100 mM and 1 mM. Spraying should be done when the plant is at a stage of growth where it bears two to about six true leaves, preferably between two and five leaves, and more preferably between three and four true leaves. In the case of dicotyledons, these numbers refer to the number of sets of leaves, and in all cases, true leaves refers the leaf number minus the cotyledons. The preferred stage of development of the last leaf which has grown is that where the size of the leaf (or sets of leaves) is between about one-third to three-quarters the size of the preceding leaf, more preferably, about one-half the size of the preceding leaf, however, positive results are achieved at any lead size as described above.

The metal ions of the present invention should be applied at the rate of between about 0.1 moles to 10,000 moles per acre, preferably in an amount between about 0.1 and 100 moles per acre. Since the amount of metal ion sprayed depends on the application rates of the final 1-triacontanol formulations and also, since different crops respond to somewhat different metal ions concentration ranges, this amount may vary somewhat. In fact, quantities of metal ions amounting to as low as 0.2 mMol per acre may be effective under appropriate conditions, but would not be preferred due to the nature of modern equipment used in the application process.

Typically, the amount of 1-triacontanol applied should be at least about 0.1 mg per acre to the area where plants are grown, but more advantageously, between 5 and 20 mg per acre. Since the purity of the 1-triacontanol used somewhat influences the amounts required, 1-triacontanol of extremely high purity may be applied at lower rates per acre, and that of lesser purity may require higher application rates. A convenient and inexpensive synthetic route to obtain high purity 1-triacontanol is disclosed in U.S. Pat. No. 4,167,641, issued Sept. 11, 1979 to the present inventor.

The present invention may also be carried out by application of the metal ions directly to the soil or the growing medium where plants are growing, however, much larger quantities of the metal ions are required. Also, the metal ions must be applied at a stage before application of the 1-triacontanol formulations in order that the ions may be suitably absorbed by plant life for the formulations to become effective. For example, between about 5 molar and 1 mM solutions of the metal ion salts may be applied to the soil in an amount to supply each plant with between about ten and 1,000 times the amount of metal ion required when application of the formulations is made through foliar spraying.

The metal salts of the invention which are useful are any metal salts which release metal ions having a valence of +2 or more, with inorganic salts being preferred. The ionic radii of the metal ions of the present invention are preferably between about 0.6 and 1.5 angstroms, more preferably between 0.7 and 1.5 angstroms, and most preferably between about 0.95 and 1.3 angstroms. While other metal ions are useful, having a valence of +2 or more, the preferred metal ions show superior results, as will become apparent in the following examples. Also, aquated metal ions in aqueous solutions show excellent results.

The preferred metal ions of the invention, along with their ionic radii, are listed below:

| Ion | Avg. Radius (Å) | Ion | Avg. Radius (Å) |
|---|---|---|---|
| $Ca^{+2}$ | 1.08 | $Mn^{+2}$ | 0.88 |
| $Sr^{+2}$ | 1.24 | $La^{+3}$ | 1.10 |
| $Ba^{+2}$ | 1.42 | $Ce^{+4}$ | 0.94 |
| $Cd^{+2}$ | 1.05 | $Mg^{+2}$ | 0.77 |
| $Pb^{+2}$ | 1.19 | $Zn^{+2}$ | 0.74 |
| $Co^{+2}$ | 0.72 | $Cu^{+2}$ | 0.96 |

The ionic radii of other metal ions which may be effectively used in the formulations of the present invention, having a valence of +2 or more, are included below:

| Ion | Avg. Radius (Å) | Ion | Avg. Radius (Å) |
|---|---|---|---|
| $Ce^{+3}$ | 1.034 | $Hg^{+2}$ | 1.10 |
| $Co^{+3}$ | 0.63 | $In^{+3}$ | 0.81 |
| $Cr^{+3}$ | 0.63 | $Lu^{+3}$ | 0.93 |
| $Er^{+3}$ | 0.881 | $Mo^{+4}$ | 0.70 |
| $Eu^{+2}$ | 0.950 | $Ni^{+2}$ | 0.69 |
| $Eu^{+3}$ | 0.950 | $Nd^{+3}$ | 0.995 |
| $Fe^{+2}$ | 0.74 | $Pa^{+5}$ | 0.89 |
| $Fe^{+3}$ | 0.64 | $Pa^{+4}$ | 0.84 |
| $Gd^{+3}$ | 0.938 | $Pm^{+3}$ | 0.979 |
| $Hf^{+4}$ | 0.78 | $Pr^{+3}$ | 1.013 |
| $Pr^{+4}$ | 0.90 | $Tm^{+3}$ | 0.87 |
| $Sm^{+3}$ | 0.964 | $V^{+2}$ | 0.88 |
| $Sm^{+2}$ | 0.93 | $V^{+3}$ | 0.74 |
| $Tb^{+3}$ | 0.923 | $Y^{+3}$ | 0.893 |
| $Tb^{+4}$ | 0.84 | $Yb^{+2}$ | 0.93 |
| $Ti^{+2}$ | 0.94 | $Yb^{+3}$ | 0.858 |
| $Ti^{+3}$ | 0.76 | $Zr^{+4}$ | 0.79 |

Metal ions having a valence of +2 or more are most effective. Other ions other than those listed above may be expected to show similar synergistic effects in the 1-triacontanol formulations of the present invention. While a number of the ions are toxic to animal life, such as lead, these are extremely useful when applied to plant life such as trees, ornamentals, and field corn or sugar beets which would be used in the production of ethyl alcohol for fuel and other purposes.

Of the metal ions listed, the most useful are $Ca^{+2}$ and $Mg^{+2}$ since they exhibit low toxicity are naturally-occurring, however, other ions are equally effective and also have low toxicities, some of which show an abundance in nature. Furthermore, ions such as $Ca^{+2}$ ($CaCl_2$) have the advantage of being exempt from the requirements of tolerances by the U.S. Environmental Protection Agency. Therefore, the most preferred metal ions from Group II of the periodic table are $Mg^{+2}$ and $Ca^{+2}$, however, $Ba^{+2}$ and $Sr^{+2}$ produce excellent synergistic results. Of the lanthanides, another preferred class of compounds, $La^{+3}$ and $Ce^{+4}$ are preferred, but others are expected to show similar results. Many transition elements are very useful, some of which show high toxicities in mammals, such as lead and cadmium, but are valuable on crops and plants not utilized for food purposes. It may be concluded that all metal ions of +2 valence or more are valuable in the 1-triacontanol formulations of the present invention, since such a diverse variety of metal ions are shown to be effective.

The preferred metal ion, due to low cost, low toxicity, and natural abundance, is $Ca^{+2}$, and this metal ion was used to evaluate the effects of the 1-triacontanol formulations on a large variety of plants contained in the present invention. Positive results are obtained with a large variety of crops, such as sweet corn, field corn, tomatoes, peas, beans, lettuce, soybeans, wheat, barley, rice, carrots, radishes, cucumbers, asparagus, and other crops. In the absence of the metal ions, however, only sweet corn was found to give reproducible increases which averaged about 20%, while other crops tested without the addition of the metal ions showed no significant increases. Similarly, the formulations of the prior art, disclosed in U.S. Pat. No. 4,150,970 by Ries, et al., were found to show eratic increases in the trials conducted here, and showed decreases in dry weight increases of the seedlings treated with these formulations when $Ca^{+2}$ was combined in the formulations, presumably due to complex formation with the surfactant additive.

It has also been discovered that plants respond to different ranges of concentrations of the metal ions, and concentrations in excess of the optimum concentration for a particular plant causes an inhibition of activity of the formulations of the present invention. The usual effective range of metal ions is up to about ten-fold the concentration required for a minimal effect, however, this depends somewhat on the crop or plant being tested. For example, formulations containing $Ca^{+2}$ or $La^{+3}$ are effective on field corn at a low concentration and narrow range of concentrations, and soybeans show a similar effect.

While not wishing to be bound by the following mechanism whereby the invention achieves its outstanding results over the prior art, it is possible that calcium, a necessary plant electrolyte, may be required for the activity of 1-triacontanol.

The formulations of the present invention also show utility as agents which counteract the effects of herbicidal compounds, such as synthetic auxins, antiauxins, and the like. Alterations in the compositions, may therefore be made to selectively protect plant life from herbicides, and may serve to increase the growth of the plant life upon which the herbicidal agent acts. Thus, application of the formulations of the invention may be used to counteract the effects of agents, such as phenoxyacetic acids and their derivatives, or cause an increase in the growth of the dicotyledonous plant life upon which they act, rather than plant death. Many alterations in compositions of the formulations of the present invention, therefore, will be apparent to those skilled in the art as a result of the detailed description contained herein which may be suited to a number of purposes.

Seed obtained from generations of plants which have been sprayed with the formulations of the invention are found to be of significantly larger size than those obtained from unsprayed plants of the same generation. When these seeds are planted, an increase is observed over the growth observed with the second generation control seeds without further application of the formulations. In addition, spraying subsequent generations with the formulations contained in the present invention show an additive increase in growth. This fact shows the possibility, for the first time, of increasing crop yields or other plant growth to a very high degree through the spraying of the formulations on successive generations of plant life. This innovation is highly applicable to increasing world food supplies, lumber supplies, fuels obtained from plant life (such as ethanol, etc.), and the like.

Other long-chain alcohols are biologically active when applied to plant life, however, none of these naturally-occurring compounds are found to show the growth-promoting effect observed with 1-triacontanol (see Jones, et al., Planta, 144: 277 (1979)). It is therefore also likely that the formulation of these alcohols using the methods of the present invention may enhance their respective activities with regard to plant growth, whether stimulatory, inhibitory, or other action, and not beyond the scope of the present invention.

The invention being thus described, other objects and further scope of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 3 is a graph showing the increases in the marketable yield of beans at different time intervals.

FIG. 4 is a graph showing the increases in the marketable yield of tomatoes at different time intervals.

BEST MODE OF THE INVENTION

Examples

Figure 1A:
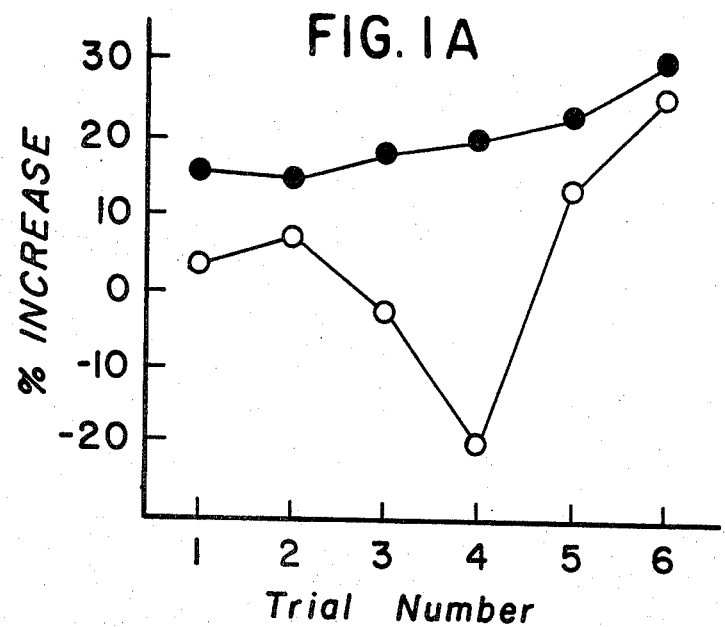
FIG. 1A represents increases in dry weight and FIG. 1B, increases in water uptake.

The following examples are presented herein as being exemplary of the present invention and, accordingly, should not be considered in anyway as being limitative of the applicant's inventive contribution.

EXAMPLE 1

A 1 mg quantity of 1-triacontanol was dissolved in 20 ml of acetone or methyl ethyl ketone at the boiling point, and the solution was cooled to room temperature. The solution may be further diluted with the ketone as desired to achieve a lesser 1-triacontanol concentration. The above solution was then diluted to one liter with water at room temperature, and the final solution was adjusted, as required, to a pH of 8 or more. For practical application to plant life in the field, 50 to 200 mg of 1-triacontanol may be dissolved in one U.S. gallon (3.79 liters) of solvent and suitably diluted with water at a pH of 8 to 10 to cover 5 to 20 acres of land, respectively, by foliar application.

EXAMPLE 2

A 10 mg quantity of 1-triacontanol was dissolved in 100 ml of methanol (or 50 ml of ethanol) at the boiling point. The mixture was diluted to one liter with water with vigorous stirring at room temperature. The concentrate may also be diluted with solvent to attain a lower 1-triacontanol concentration, and applied as described under Example 1.

EXAMPLE 3

One mg of 1-triacontanol was dissolved in 25 ml of hot isopropanol, and the hot solution was poured into 975 ml of water with vigorous stirring over a one minute period. Alternately, a lesser amount of 1-triacontanol (e.g., 0.1 mg) may be added to the polar organic solvent, and the stable concentrate may subsequently be diluted to one liter with water (pH 8 or greater) giving a solution having a 1-triacontanol concentration of 0.1 mg/l. This solution may be applied in the same manner as described under Example 1.

EXAMPLE 4

One mg or less of 1-triacontanol was dissolved in 25 ml of hot diethylene glycol and added to 975 ml of water with rapid stirring. The resulting solution may then be used as described above.

EXAMPLE 5

One mg of 1-triacontanol was dissolved in 10 ml of hot n-butyl alcohol with stirring, and the mixture was stirred into 990 ml of warm water. The cooled solution was used as described above.

EXAMPLE 6

Up to ten mg of 1-triacontanol was dissolved in 100 ml of warm dioxane and the solution was added over 60 seconds to 900 ml of water. The solution may be used as previously described.

EXAMPLE 7

One mg of 1-triacontanol was dissolved in 50 ml of hot propylene glycol and added to 950 ml of water with stirring. The solution may be used as described above.

EXAMPLE 8

One mg of 1-triacontanol (or between 0.1 and 10 mg) was dissolved in 20 ml of hot dimethyl sulfoxide (DMSO) and cooled to room temperature. The resultant solution was diluted to 980 ml with water and used as described under Example 1.

COMPARATIVE RESULTS

Pure 1-triacontanol was prepared in accordance with U.S. Pat. No. 4,167,641, starting with stearic acid of a purity of 97–99% or greater, and repeating the sequence disclosed therein twice. The product had a melting point of at least 87° C. and showed no traces of carbonyl compound impurities or other long-chain alcohol contaminants. Indole-3-acetic acid, naphthalene acetic acid, gibberellic acid (potassium salt), and kinetin were purchased from Calbiochem-Behring Corporation, La Jolla, Calif. 2,4-Dichlorophenoxyacetic acid, 2,3,5-triiodobenzoic acid, and maleic hydrazide were obtained from Aldrich Chemical Company, Milwaukee, Wis. All metal salts and solvents used were of reagent grade.

Sweet corn seed (cv. Silver Queen and cv. Early Sunglow) cucumber seed (cv. Straight Eight), watermelon seed (cv. Dixie Queen), bean seed (cv. Blue Lakes), and radish seed (cv. Champion) were the product of the Wetzel Seed Co., Harrisonburg, Va. Cucumber seed (cv. Improved White Spine), carrot seed (cv. Imperator), lettuce seed (cv. Iceberg), and cherry tomato seed (cv. Red Cherry) were obtained from W. Atlee Burpee Seed Co., Riverside, Calif. Field corn seed (WF9 X Bear 38) was from the Bear Hybrid Seed Co., Decatur, Ill. Pea seed (cv. Dark Skin), sweet corn seed (cv. Jubilee), and bean seed (cv. Early Bird) were generously supplied by Western Chemical Corporation. Soybean seed (cv. Prize and cv. Williams), field corn seed (cv. TX 660), barley seed (cv. Brrsoy), asparagus seed (cv. Mary Washington), alfalfa seed (cv. Kansas), and pea seed (cv. Little Marvel) were the products of Meyer Seed Co., Baltimore, Md. Field corn seed (cv. Pioneer 3780), winter wheat seed (cv. Augusta), and rice seed (cv. ESD-7-1), were a gift of Dr. Stanley K. Ries, Michigan State University, East Lansing, Mich. Field corn seed (cv. Trojan TXS 94) was obtained from Pfizer Genetics, Olivia, Minn. Tomato seed (cv. Ponderosa Red Beefsteak) was from the Ferry Morse Seed Co., Fulton, Ky.

Original work was performed under artificial light as described in U.S. Ser. No. 202,705, filed Oct. 30, 1980. Confirming trials and subsequent experiments were performed using the following general procedure. All field trials were performed using using standard techniques described hereinafter.

Randomized complete block designs were used with the number of replications shown in Table 1. In general, greenhouse trials were conducted as follows: eight to twelve seeds were sown per pot in Peat-Lite ® Mix and received an average of 100 ml of water per day. The day after shoots emerged, seedlings were fertilized with the fertilizers listed in Table 1 (0.5 g/200 ml). After plants had the third true leaf (average), the various formulations were applied to the leaves as a fine mist at air temperatures listed in Table 1. Temperatures above 20° C., preferably 25°–30° C. are preferred.

The 1-triacontanol formulation most generally used consisted of a concentrate containing 5 mg of 1-triacontanol dissolved in 1 liter of acetone, with 20 ml of the concentrate being further dissolved to 1 liter with water having a pH between 8 and 10, with over a pH of 11 also being effective. The pH was adjusted with aqueous NaOH and the concentrate added just prior to spraying.

When other plant growth substances were added to the formulations, these were added either to the concentrate in the polar organic solvent or alternatively in the aqueous solution, depending on the solubility of the plant growth substance. All metal salts were added to the water used to spray the 1-triacontanol formulations. After spraying, preferably about four to nine days or more, plants were harvested with roots, and fresh weights were obtained. Plants were then dried in an oven, preferably at a temperature below 100° C., until constant weight was obtained, and dry weight values were obtained for each plot. Subtraction of the dry weights from the fresh weights gave the water uptake weights (water content) of each plot. The weights of the above mentioned seedlings were compared to the control weights to obtain the percent increases.

It is particularly advantageous to arrange each of the potted plants in size range categories corresponding to the number of replications used. For example, if five replications are employed, plants are divided into five size categories, normally measured by the height of the plants. Treatments are then assigned randomly within each block (size category). This removes the variation due to plant size for statistical purposes, as is well practiced in the art. The resulting data is analyzed using any appropriate means, which may include the least significant difference method (L.S.D. method), Duncan's multiple range test, as used here (Biometrics, 11:1 (1955)), or other means.

The following formulations are exemplary of those within the scope of the present invention, however, are not limited thereto.

FORMULATION 1

A 0.1 mg quantity of 1-triacontanol was dissolved in 1 ml of chloroform and shaken prior to used with one liter of water which containing 1 gram (0.1%) of Tween-20 (Example II in the U.S. Pat. No. 4,150,970 of Ries, et al.).

FORMULATION 2

A 0.1 mg quantity of 1-triacontanol was dissolved in 20 ml of acetone at 50° C., and the resultant solution, which had an indefinite shelf life, was dissolved in 980 ml of water at room temperature with stirring and/or shaking.

FORMULATION 3

A 0.1 mg quantity of 1-triacontanol was dissolved in 50 ml of hot ethanol, and the resultant solution was dissolved in 950 ml of water.

FORMULATION 4

An amount of 1-triacontanol up to 1 mg was dissolved in 20 ml of acetone at a temperature of 50° C. to form a concentrate. The concentrate was diluted with 980 ml of water having a specific metal ion concentration, with vigorous stirring or shaking.

FORMULATION 5

An amount of 1-triacontanol up to 1 mg was dissolved in 20 ml of acetone at a temperature of 50° C. to form a concentrate. The concentrate was added to 980 ml of water containing a specified amount of a water-soluble plant growth substance.

FORMULATION 6

An amount of 1-triacontanol up to 1 mg was dissolved in 20 ml of acetone at a temperature of 50° C. to form a concentrate. The concentrate was further diluted with 20 ml of water, and a specified amount of a plant growth substance was added. The resultant solution was diluted to one liter with water.

FORMULATION 7

An amount of 1-triacontanol up to 1 mg was dissolved in 20 ml of acetone at a temperature of 50° C. to form a concentrate. A specified quantity of a plant growth substance was added to the concentrate, and the resultant solution was diluted with 980 ml of water.

FORMULATION 8

An amount of 1-triacontanol up to about 0.5 mg was dissolved in 20 ml of dioxane at a temperature of 60° C., and the resultant concentrate was diluted to one liter for use.

FORMULATION 9

An amount of 1-triacontanol up to about 0.5 mg was dissolved in 25 ml of propylene glycol at a temperature of about 90° C. to form a concentrate, which was further diluted with 975 ml of water for use.

FORMULATION 10

A quantity of 1-triacontanol up to about 0.5 mg was dissolved in 20 ml of hot dimethyl sulfoxide (DMSO) and cooled to room temperature. The resulting solution was diluted to one liter with water prior to use.

FORMULATION 11

A 0.1 mg quantity of 1-triacontanol was dissolved in 1 ml of chloroform, and the solution was shaken with one liter of water containing 1 gram (0.1%) of Tween-20 and a specified quantity of a metal salt.

FORMULATION 12

A 100 mg quantity of 1-triacontanol was dissolved in one U.S. gallon of acetone at the boiling point to form a stable concentrate (TRIACON-10 TM). The concentrate was diluted with water which optionally contained a specified metal ion concentration and a pH over about 8 at the rate of one U.S. gallon (3.79 liters) to between fifty and four hundred U.S. gallons of water, and applied to ten acres of crop land.

FORMULATION 13

A 200 mg quantity of 1-triacontanol was dissolved in one U.S. gallon of acetone at the boiling point to form a concentrate (TRIACON-20 TM). The concentrate was diluted with rapid stirring in water which optionally contained a specified metal ion concentration and a pH over about 8 at the rate of one U.S. gallon of concentrate to between twenty-five and eight hundred U.S. gallons of water.

FORMULATION 14

One to 100 mg of 1-triacontanol is dissolved or suspended in a polar organic solvent, and the resulting solution is added to a solution or suspension of a calcium (or other metal ion) salt having a limited solubility. The solution or suspension may further be admixed with inert ingredients known in the art which affect the adhesion of foliarly applied compounds to plant life. The resulting mixture is applied to plant life to counteract the effects of herbicidal agents in order that desired plant life be not affected thereby.

Field trials were conducted in Northern Virginia on plots that were replicated at least five times. Plots consisted of single rows of plants in blocks of three or more plots, with treatments being assigned randomly within each block. Plants were generally sprayed at about the three leaf stage (or three sets of leaves for dicotyledons), however, soybeans, showed better results when sprayed at the four leaf stage (third set of three leaves).

Plants were fertilized with the fertilizers described in Table 1, sprayed at air temperatures listed in the same Table. Spraying was usually avoided under windy conditions to avoid drift. In the examples set forth herein, data were treated in a similar manner to those found in the greenhouse trials, with analysis of variance performed for each trial, and the use of a suitable statistical method for the analysis of results, preferably Duncan's multiple range test.

Upon analysis of the greenhouse data, it becomes apparent that the results found in the field generally correlate well with the dry weight increases observed in the greenhouse trials. This offers a convenient method to optimize results for various crops between or during growing seasons. It also appears that the increases observed in dry weight in the greenhouse trials using the formulations of the present invention are approximately equal to the marketable yield increases of crops in the field for monocots, however, the greenhouse data for dicotyledons shows about one-half the increases as may be observed under field conditions. For example, a 40% increase in dry weight of a vegetable crop in the greenhouse indicates a possible marketable yield increase of up to about 80% under field conditions. Further evidence of this fact will become clear in the following examples of the invention.

TABLE 1

Fertilizers Used, Spraying Temperatures, and Numbers of Replications in Greenhouse and Field Trials.

| CROP | GREENHOUSE | | | FIELD TRIALS | | |
|---|---|---|---|---|---|---|
| | TEMP. | FERT. | REPS. | TEMP. | FERT. | REPS. |
| Peas | 25° C. | 15-30-15 | 5 | 25° C. | 10-6-4 | 5 |
| Wheat | 23° | 15-30-15 | 6 | — | — | — |
| Radishes | — | — | — | 25° | 18-18-21 | 6 |
| Watermelons | 27° | 15-31-15 | 5 | — | — | — |
| Beans | — | — | — | 30° | 10-6-4 | 5 |
| Carrots | 25° | 15-30-15 | 5 | — | — | — |
| Sweet Corn: | | | | | | |
| "Early Sunglow" | — | — | — | 27° | 10-6-4 | 5 |
| "Silver Queen" | 25° | 15-30-15 | 5 | 30° | 10-6-4 | 5 |
| "Jubilee" | — | — | — | 27° | 10-6-4 | 5 |
| Soybeans | 27° | 15-30-15 | 5 | 27° | 10-6-4 | 5 |
| Cucumbers | — | — | — | 27° | 5-10-5 | 5 |
| Lettuce | — | — | — | 27° | 15-30-15 | 5 |
| Tomatoes: | | | | | | |
| "Red Cherry" | — | — | — | 30° | 5-10-5 | 5 |
| "Beefsteak" | 27° | 15-30-15 | 5 | 30° | 5-10-5 | 5 |
| Field Corn: | | | | | | |
| "Trojan TXS 94" | 25–30° | 15-30-15 | 5 | 30° | 10-6-4 | 5 |
| "Pioneer 3780" | 31° | 15-30-15 | 5 | — | — | — |
| "WF9 X Bear 38" | 25° | 15-30-15 | 5 | — | — | — |
| "TX 660" | 25° | 15-30-15 | 5 | — | — | — |
| Barley | 25° | 15-30-15 | 4 | — | — | — |
| Rice | 25° | 15-30-15 | 5 | — | — | — |

TABLE 1-continued

Fertilizers Used, Spraying Temperatures, and Numbers of Replications in Greenhouse and Field Trials.

| CROP | GREENHOUSE | | | FIELD TRIALS | | |
|---|---|---|---|---|---|---|
| | TEMP. | FERT. | REPS. | TEMP. | FERT. | REPS. |
| Asparagus | 25° | 15-30-15 | 4 | — | — | — |
| Alfalfa | 25° | 15-30-15 | 6 | — | — | — |

TABLE 2

Increases in the Dry Weight and Water Uptake of 14-Day Old Hybrid Sweet Corn Seedlings (cv. Silver Queen) Sprayed with Formulations of 1-Triacontanol (0.1 mg/l), without the Addition of Metal Ions or Other Plant Growth Substances (pH 8 to 9).

| FORMU-LATION NUMBER | PERCENT INCREASES | | LEVEL OF SIGNIFICANCE | |
|---|---|---|---|---|
| | DRY WT. | $H_2O$ UPTAKE | DRY WT. | $H_2O$ UPTAKE |
| 1 | −19% | −8% | 0.005 | 0.05 |
| 1 | +10 | −10 | 0.07 | 0.07 |
| 2 | +21 | +16 | 0.005 | 0.005 |
| 2 | +19 | +29 | 0.06 | 0.02 |
| 2 | +36 | +19 | 0.01 | 0.08 |
| 3 | +19 | +6 | 0.06 | N.S. |
| 8 | +17 | +8 | 0.07 | N.S. |
| 9 | +33 | +20 | 0.002 | 0.03 |
| 10 | +18 | −9 | 0.02 | N.S. |

TABLE 3

Increases in the Dry Weight and Water Uptake of 14-Day Old Hybrid Sweet Corn Seedlings (cv. Silver Queen), over Controls, Sprayed with a Variety of Plant Growth Substances, with and without the Addition of 1-Triacontanol (0.1 mg/liter).

| PLANT GROWTH SUBSTANCE | CONCEN-TRATION (mM) | TRIACON-TANOL* | INCREASES | | | |
|---|---|---|---|---|---|---|
| | | | DRY WT. | P | $H_2O$ UPTAKE | P |
| IAA | 0.01 | − | +4% | N.S. | −7% | N.S. |
| IAA | 0.01 | + | +2 | N.S. | −5 | N.S. |
| $GA_3$ | 0.01 | − | −24 | 0.01 | −6 | N.S. |
| $GA_3$ | 0.01 | + | −15 | 0.01 | −3 | N.S. |
| Kinetin | 0.01 | − | −24 | 0.01 | −3 | N.S. |
| Kinetin | 0.01 | + | −21 | 0.01 | +14 | 0.01 |
| 2,4-D | 0.01 | − | +10 | 0.05 | −9 | 0.05 |
| 2,4-D | 0.01 | + | +17 | 0.01 | −13 | 0.05 |
| TIBA | 0.10 | − | +10 | 0.05 | −12 | 0.05 |
| TIBA | 0.10 | + | +19 | 0.01 | +1 | N.S. |
| MH | 0.10 | − | +7 | N.S. | −1 | N.S. |
| MH | 0.10 | + | +12 | 0.05 | −7 | N.S. |
| — | — | + | +20 | 0.01 | +16 | 0.01 |

*Formulation 7 is used in all examples above except in the cases of $GA_3$ (Formulation 5), the control without the addition of plant growth substances (Formulation 2), and the formulations containing MH (formulation 6).

TABLE 4

Increases in the Dry Weight and Water Uptake of 14-Day Old Hybrid Sweet Corn Seedlings (cv. Silver Queen), over Controls, Sprayed with a Variety of Metal Salts and Formulations, with and without the Addition of 1-Triacontanol (0.1 mg/liter).

| METAL SALT | CONCEN-TRATION (mM) | TRIACON-TANOL | FORMU-LATION | INCREASES | | | |
|---|---|---|---|---|---|---|---|
| | | | | DRY WT. | P | $H_2O$ UPTAKE | P |
| $CaCl_2$ | 10 | − | 4 | +4% | N.S. | −2% | N.S. |
| $CaCl_2$ | 10 | + | 4 | +65 | 0.01 | +11 | 0.05 |
| $CaCl_2$ | 5 | + | 4 | +50 | 0.01 | +21 | 0.05 |
| $CaCl_2$ | 1 | + | 4 | +42 | 0.01 | +35 | 0.01 |
| $CaCl_2$ | 10 | + | 11 | −5 | N.S. | +9 | N.S. |
| $CaCl_2$ | 5 | + | 11 | +5 | N.S. | +6 | N.S. |
| $LaCl_3$ | 10 | − | 4 | +5 | N.S. | −2 | N.S. |
| $LaCl_3$ | 10 | + | 4 | +72 | 0.01 | +18 | 0.01 |
| $Ce(SO_4)_2$ | 1 | + | 4 | +21 | 0.01 | +26 | 0.01 |
| $MgCl_2$ | 1 | + | 4 | +21 | 0.01 | +20 | 0.01 |
| $MgCl_2$ + $CaCl_2$ | 1 ea. | + | 4 | +39 | 0.01 | +30 | 0.01 |
| $MnCl_2$ | 1 | + | 4 | +9 | N.S. | +29 | 0.01 |
| — | — | + | 1 | +20 | 0.01 | +16 | 0.01 |

TABLE 5

Increases in the Dry Weight and Water Uptake of 14-Day Old Hybrid Sweet Corn Seedlings (cv. Silver Queen), over Controls, Sprayed with a Variety of Metal Ions (9 mM) and 1-Triacontanol (0.1 mg/liter) at pH 8 to 10 using Formulation 4.

| METAL ION | DRY WEIGHT* | % INCREASE | WATER UPTAKE* | % INCREASE |
|---|---|---|---|---|
| CONTROL | 0.86 g | — | 8.7 g | — |
| $Ca^{+2}$ | 1.29 | +50% | 10.1 | +16% |
| $Ba^{+2}$ | 1.16 | +35 | 12.9 | +48 |
| $Sr^{+2}$ | 1.56 | +81 | 12.9 | +48 |
| $Mg^{+2}$ | 1.49 | +73 | 13.5 | +55 |
| $Mn^{+2}$ | 1.13 | +31 | 10.9 | +25 |
| $Cd^{+2}$ | 1.36 | +58 | 9.9 | +14 |
| $Pb^{+2}$ | 1.56 | +81 | 13.5 | +55 |
| $Zn^{+2}$ | 1.17 | +38 | 10.5 | +21 |
| — | 1.04 | +21 | 10.1 | +16 |

TABLE 6

Increases in Crop Yields Observed Spraying Two Different Formulations in the Field without the Addition of Metal Salts or Other Plant Growth Substances, Using 1 mg/l of 1-Triacontanol.

| CROP | FORMULATION | INCREASE PER ACRE |
|---|---|---|
| Hybrid Sweet Corn | 1 | $-24\%^a$ |
| 'Silver Queen' | 2 | +21 |
| Beans | 1 | +29 |
| 'Blue Lakes Stringless'[b] | 2 | +60 |
| Cucumbers | 1 | −10 |
| 'Straight Eight'[b] | 2 | +39 |

[a]Results were significant at better than the 0.05 level.
[b]Increases characterized by a greater number of beans or cucumbers, which resulted in an increase in total fresh weight.

TABLE 7

Increases in the Marketable Yield of Sweet Corn with Cultivars Sprayed with Formulations of 1-Triacontanol and $CaCl_2$ during the 1981 Growing Season.*

| CULTIVAR | $CaCl_2$ (mM) | TRIACONTANOL | PH | PERCENT INCREASE | LEVEL OF SIGNIFICANCE |
|---|---|---|---|---|---|
| "Early Sunglow" | 0 | 0.00 mg/l | 9.8 | — | — |
|  | 10 | 0.25 | 9.8 | +47% | 0.05 |
| "Jubilee" | 0 | 0.00 | 9.7 | — | — |
|  | 5 | 0.25 | 9.7 | +44 | 0.05 |
| "Silver Queen" | 0 | 0.00 | 10.4 | — | — |
|  | 9 | 0.25 | 10.4 | +49 | 0.01 |

*Field trial data for 1980 showed significant increases in three out of three trials for the Silver Queen cultivar, ranging from 51 to 54%.

TABLE 8

Increases in the Dry Weight and Water Uptake of Field Corn Seedlings Sprayed with Formulations of 1-Triacontanol (Formulations 4 & 11, 0.1 mg/liter) with without the Addition of Metal Ions.

| METAL SALT | CONCENTRATION (mM) | FORMULATION | INCREASES* DRY WT. | p | WATER UPTAKE | p |
|---|---|---|---|---|---|---|
| "Trojan TXS 94" | | | | | | |
| $CaCl_2$ | 1 | 4 | +20–30% | 0.01 | +21% | 0.01 |
| $CaCl_2$ | 1 | 11 | −10 | N.S. | −19 | 0.01 |
| $CaCl_2$ | 0.5 | 4 | +22 | 0.01 | +8 | N.S. |
| $CaCl_2$ | 1.25 | 4 | +30 | 0.01 | +9 | 0.05 |
| $LaCl_3$ | 1 | 4 | +25–32 | 0.01 | +25 | 0.01 |
| $CaCl_2$ + $MgCl_2$ | 1 ea. | 4 | +20–30 | 0.01 | +6–18 | 0.05 |
| — | — | 4 | −3 | N.S. | −4 | N.S. |
| — | — | 11 | −8 | N.S. | −26 | 0.01 |
| "Pioneer 3780" | | | | | | |
| $CaCl_2$ | 1 | 4 | +19 | 0.01 | +9 | 0.05 |
| $CaCl_2$ | 0 | 11 | −5 | N.S. | +8 | 0.05 |
| "WF9 X Bear 38" | | | | | | |
| $CaCl_2$ | 1 | 4 | +8 | 0.13 | +5 | N.S. |

*Increases over controls sprayed with solvent alone.

TABLE 9

Differences in the Lengths of Stems (to the First Leaf, Length "a") and Total Plant Length (Length "b"), over Controls, of Hybrid Sweet Corn Seedlings (cv. Silver Queen) Sprayed Day 7 with a Variety of Plant Growth Substances, with and without the Addition of 1-Triacontanol (0.1 mg/liter), "T".

| PLANT GROWTH SUBSTANCE | LENGTH "a" | INCREASE | LENGTH "b" | INCREASE |
|---|---|---|---|---|
| IAA | 11.6 cm | 0% | 24.4 cm | −2% |
| IAA + T | 12.6 | +10 | 29.8 | +19 |
| $GA_3$ | 11.2 | −3 | 26.6 | +6 |
| $GA_3$ + T | 13.0 | +13 | 32.5 | +30 |
| Kinetin | 11.5 | 0 | 32.5 | +30 |
| Kinetin + T | 11.5 | 0 | 25.0 | 0 |
| $CaCl_2$ + T | 11.7 | +2 | 27.5 | +10 |
| T Alone | 11.5 | 0 | 28.8 | +15 |
| Control | 11.5 | — | 25.0 | — |

Note:
These data are presented to indicate in the geometry of seedling growth when sprayed with various plant growth substances and do not reflect actual increases in tissue growth, which would be indicated by increases in weight.

TABLE 10

Comparison of the Effects of Spraying Hybrid Sweet Corn Seedlings with Formulations of 1-Triacontanol (0.1 mg/liter, Formulation 4) with and without the Addition of $CaCl_2$ and Metal Complexes (9 mM).

| Formulation Additive | Increase in Dry Weight | Level of Significance |
|---|---|---|
| $CaCl_2$ | +50% | 0.01 |
| Metal Proteinate[a] | +15 | N.S. |
| $Co(NH_3)_6Cl_3$ | +13 | N.S. |

TABLE 10-continued

Comparison of the Effects of Spraying Hybrid Sweet Corn Seedlings with Formulations of 1-Triacontanol (0.1 mg/liter, Formulation 4) with and without the Addition of $CaCl_2$ and Metal Complexes (9 mM).

| Formulation Additive | Increase in Dry Weight | Level of Significance |
|---|---|---|
| No Additive | +21 | 0.05 |

<sup>a</sup>The metal proteinate consisted of a complex of calcium with two equivalents of L-leucine in accordance with U.S. Pat. No. 4,169,717 to Ashmead.

TABLE 11

Increases in the Dry Weight and Water Uptake of Tomato Seedlings (cv. Ponderosa Red Beefsteak), over Controls, Sprayed with 1-Triacontanol (0.1 mg/liter) on the 36th Day after Germination and Harvested on the 45th Day, Using Different Formulations.

| $CaCl_2$ (mM) | FORMU-LATION | INCREASES DRY WT. | p | $H_2O$ UPTAKE | p |
|---|---|---|---|---|---|
| 5 | 4 | +38% | 0.01 | +34% | 0.01 |
| 10 | 4 | +43 | 0.01 | +10 | 0.05 |
| 10 | 11 | −1 | N.S. | −5 | N.S |
| 2.5 | 11 | +2 | N.S. | +2 | N.S. |
| — | 4 | −3 | N.S. | −2 | N.S. |
| — | 11 | +6 | N.S. | −4 | N.S. |

TABLE 12

Increases in the Marketable Yield of Tomatoes Using Formulation 12 Containing 0.25 mg/liter of 1-Triacontanol in 1981 Field Trials (pH 9 to 10).

| CULTIVAR | $CaCl_2$ (mM) | FRESH WEIGHT (gms) | PERCENT INCREASES | LEVEL OF SIGNIFICANCE |
|---|---|---|---|---|
| "Ponderosa Red Beefsteak"* | 5 | 15353 g | +38% | 0.10 |
| "Red Cherry" | 5 | 5679 | +26 | 0.06 |

*Field trials the previous year showed an increase of 67 to 72%, which was significant at the 0.01 level.

TABLE 13

Increases in the Dry Weight of Pea Seedlings Treated with Formulation 4 Containing 0.1 mg/liter of 1-Triacontanol and Varying Concentrations of $CaCl_2$. Weights are the Sum of Four Plants.

| $CaCl_2$ (mM) | DRY WT. (gm) | PERCENT INCREASES | LEVEL OF SIGNIFICANCE |
|---|---|---|---|
| "Dark Skin" | | | |
| 0.0 | 0.79 | −5% | N.S. |
| 1.0 | 0.84 | +1 | N.S. |
| 3.0 | 0.77 | −7 | N.S. |
| 5.0 | 0.89 | +7 | N.S. |
| 7.0 | 0.86 | +3 | N.S. |
| 10.0 | 0.98 | +18 | 0.01 |
| 15.0 | 1.10 | +33 | 0.01 |

TABLE 13-continued

Increases in the Dry Weight of Pea Seedlings Treated with Formulation 4 Containing 0.1 mg/liter of 1-Triacontanol and Varying Concentrations of $CaCl_2$. Weights are the Sum of Four Plants.

| $CaCl_2$ (mM) | DRY WT. (gm) | PERCENT INCREASES | LEVEL OF SIGNIFICANCE |
|---|---|---|---|
| Control | 0.83 | — | — |

TABLE 14

Increases in the Marketable Yield of Peas (cv. Dark Skin) Using Formulation 13 Containing 0.25 mg of 1-Triacontanol/liter and Varying Concentrations of $CaCl_2$. Weights are per 12 Plants/Plot, pH 8.7.

| $CaCl_2$ (mM) | FRESH WT. (gm) | PERCENT INCREASES | LEVEL OF SIGNIFICANCE |
|---|---|---|---|
| 10 | 78 | +35% | 0.05 |
| 15 | 97 | +63 | 0.05 |
| Control | 59 | — | — |

TABLE 15

Increases in the Dry Weight of Watermelon Seedlings Sprayed with Formulation 4, Containing 0.1 mg/liter of 1-Triacontanol, $CaCl_2$, on Day 36 after Germination at pH 9.8, and Harvested on Day 45 (Weights are per four plants, cv. Dixie Queen).

| $CaCl_2$ (mM) | DRY WT (gm) | PERCENT INCREASES | LEVEL OF SIGNIFICANCE |
|---|---|---|---|
| Control | 0.61 g | — | — |
| 5 | 0.84 | +38% | 0.10 |
| 10 | 0.90 | +48 | 0.10 |

TABLE 16

Increases in the Crop Yield of Radishes (cv. Champion) Sprayed with 1-Triacontanol (0.25 mg/liter) Using Formulation 4 at pH 9.7, Not Including Foliage*

| TREATMENT | $CaCl_2$ (mM) | FRESH WT. | IN-CREASE | LEVEL OF SIGNIFICANCE |
|---|---|---|---|---|
| Control | — | 93 g | — | — |
| Triacontanol | 10 | 123 | +32% | 0.10 |

*Weights are the sum of twenty plants per plot.

TABLE 17

Increases in the Dry Weight of Winter Wheat Seedlings (cv. Augusta) Sprayed with 1-Triacontanol (Formulation 4) at pH 9.0.

| TRIACONTANOL (mg/l) | $CaCl_2$ (mM) | DRY WT.* | INCREASE | LEVEL OF SIGNIFICANCE | INCREASE (HEIGHT) |
|---|---|---|---|---|---|
| — | — | 0.513 g | — | — | — |
| 0.1 | 10 | 0.682 | +33% | 0.01 | +19 |
| 0.1 | 15 | 0.616 | +20 | 0.05 | +15 |
| 0.1 | 20 | 0.682 | +33 | 0.01 | +7 |
| 0.1 | 25 | 0.708 | +38 | 0.01 | +8 |
| 0.1 | 0 | 0.520 | 0 | N.S. | 0 |

*Dry weights are the sum of four plants per plot (average).
Water Uptake increases were found to parallel dry weight increases in the case of wheat with the same levels of significance.

TABLE 18

Increases in the Dry Weight and Water Uptake of Soybean Seedlings Sprayed with and without Various Concentrations of $CaCl_2$ and 1-Triacontanol (Formulation) No. 4) at a pH of 10.4.

| TRIACON-TANOL (mg/l) | $CaCl_2$ (mM) | INCREASES (%) DRY WT. | p | WATER UPTAKE | p |
|---|---|---|---|---|---|
| 0 | 0 | — | — | — | — |
| 0.1 | 0 | +2% | N.S. | −12% | 0.01 |
| 0.1 | 1 | +10 | 0.05 | +2 | N.S. |

TABLE 18-continued

Increases in the Dry Weight and Water Uptake of Soybean Seedlings Sprayed with and without Various Concentrations of CaCl₂ and 1-Triacontanol (Formulation) No. 4) at a pH of 10.4.

| TRIACON-TANOL (mg/l) | CaCl₂ (mM) | DRY WT. | p | WATER UPTAKE | p |
|---|---|---|---|---|---|
| 0.1 | 3 | +19 | 0.01 | +17 | 0.01 |
| 0.1 | 5 | −1 | N.S. | +3 | N.S. |

TABLE 19

Increases in the Fresh Weight of Soybean Pods and Actual Dry Weight of Soybeans Sprayed with TRIACON-10 (Formulation 12), over Controls. Plants were Sprayed with 0.15 mg/liter of 1-Triacontanol and 3 mM CaCl₂ at a pH of 9.8 at Two Different Stages of Development

| TREATMENT | No. OF SETS OF LEAVES | FRESH WT. | % | p | DRY WT. | % | p |
|---|---|---|---|---|---|---|---|
| Control | — | 1930 g | — | — | 350 g | — | — |
| Triacontanol | 3 | 2520 | +31 | 0.05 | 475 | +40 | 0.05 |
| Triacontanol | 4 | 2750 | +42 | 0.01 | 585 | +65 | 0.01 |

TABLE 20

Increases in the Marketable Yield of Beans Sprayed with TRIACON-10 ™ (Formulation 12) at a 1-Triacontanol Concentration of 0.25 mg/liter and a pH of 8 to 9 (cv. Early Bird*).

| TREATMENT | CaCl₂ (mM) | FRESH WT. | IN-CREASE | LEVEL OF SIGNIFICANCE |
|---|---|---|---|---|
| Control | — | 3595 g | — | — |
| Triacontanol | 5.0 | 5820 | +62% | 0.01 |
| Triacontanol | 7.5 | 4785 | +33 | 0.05 |

*Increases of 90% were found with cv. Blue Lakes Stringless during the previous year growing season.

TABLE 21

Increases in the Dry Weight of Carrots Sprayed with 0.1 mg/liter of 1-Triacontanol (Formulation 4), over Controls, at a pH of 10.1.

| TREATMENT | CaCl₂ (mM) | DRY WEIGHT | IN-CREASE | LEVEL OF SIGNIFICANCE |
|---|---|---|---|---|
| Control | — | 1.45 g* | — | — |
| Triacontanol | 5 | 1.90 | +31% | N.S. |
| Triacontanol | 10 | 2.76 | +90 | 0.01 |

*Weight per plot (4 plants).

TABLE 22

Increase in the Crop Yield of Field Corn (cv. Trojan TXS 94) Treated with 1-Triacontanol Formulation 12 (0.25 mg/liter 1-Triacontanol), over Controls, Sprayed at a pH of 10.4.

| TREATMENT | CaCl₂ (mM) | WT./15 EARS | INCREASE | p | WT. of SEED | INCREASE | p |
|---|---|---|---|---|---|---|---|
| Control | — | 1777 g | — | — | 1740 g | — | — |
| Triacontanol | 1 | 2356 | +33% | 0.05 | 2211 | +27% | 0.01 |

TABLE 23

Increase in the Crop Yield of Cucumbers Treated with 1-Triacontanol Formulation 12 (0.25 mg/liter of 1-Triacontanol), over Controls, Sprayed at pH 9.8*.

| TREATMENT | CaCl₂ (mM) | FRESH WT. | IN-CREASE | LEVEL OF SIGNIFICANCE |
|---|---|---|---|---|
| Control | — | 9575 g | — | — |
| Triacontanol | 5 | 17980 | +88% | 0.05 |

*The cv. used was "Improved White Spine". Results using cv. "Straight Eight" the previous year showed an increase of 101% over controls under the same conditions and a CaCl₂ concentration of 4.5 mM.

TABLE 24

Increases in the Sizes of the Seed of Crops Sprayed with Formulations of 1-Triacontanol (Formulation 12), over Controls.

| CROP | CaCl₂ (mM) | No. of SEEDS | WT. OF CONTROL SEED | WT. OF TREATED SEED | PERCENT INCREASES |
|---|---|---|---|---|---|
| SWEET CORN "Silver Queen" | 9 | 500 | 29.75 g | 43.8 | +47% |
| FIELD CORN "Trojan TXS 94" | 1 | 1000 | 252 | 297 | +18 |
| TOMATOES "Ponderosa Red Beefsteak" | 5 | 100 | 0.32 | 0.40 | +25 |
| BEANS "Early Bird" | 5 | 100 | 18.1 | 27.8 | +54 |

TABLE 25

Results of Spraying Second Generation Hybrid Sweet Corn Seedlings (cv. Silver Queen) with 1-Triacontanol Formulation 4, Containing 0.5 mg/liter of 1-Triacontanol and 10 mM $CaCl_2$ at a pH of 8.1.

| GENERATION | | INCREASES | | | |
|---|---|---|---|---|---|
| TEST SEED | CONTROL SEED | DRY WT. | p | $H_2O$ UPTAKE | p |
| SECOND (First was Sprayed Only) | SECOND (First and Second not Sprayed) | +44% | 0.01 | +40% | 0.01 |
| SECOND (First and Second Sprayed) | SECOND (First and Second not Sprayed) | +80 | 0.01 | +78 | 0.01 |
| SECOND (First and Second Sprayed) | SECOND (Second was Sprayed Only) | +41 | 0.01 | +46 | 0.01 |
| FIRST (Sprayed) | FIRST (Not Sprayed) | +44 | 0.01 | +41 | 0.01 |

RESULTS

Figure 1B:
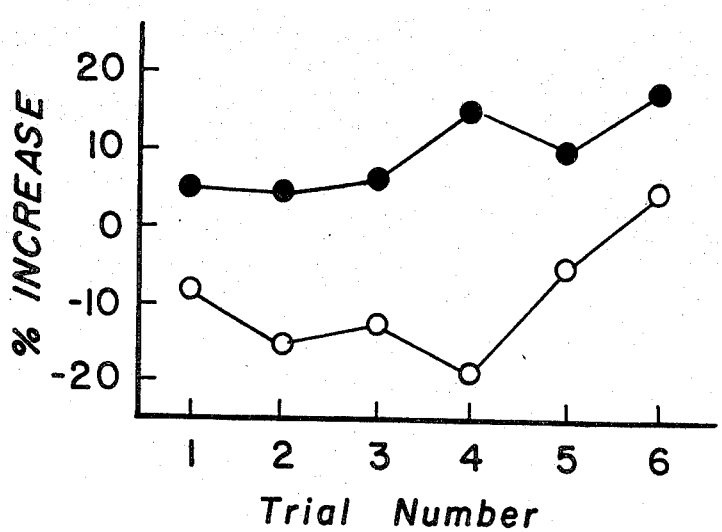
FIG. 1 is a graph showing the reproducibility in stimulating the growth of sweet corn, as determined by dry weight and water uptake increases and the formulation used, containing 0.1 mg/liter of 1-triacontanol, without the addition of metal ions. The prior art formulation (formulation 1) is compared to the formulations of the present invention (formulation 2)

Plants were grown and sprayed with the air temperatures, number of replications, and fertilizers used illustrated in Table 1. FIG. 1 and Table 2 show the consistency of the increases observed using the compositions of the present invention in relation to those using the prior art formulations (Ries, et al., U.S. Pat. No. 4,150,970). The improvements in consistency in growth increases, measured in terms of dry weight, are obvious, and are observed for several formulations when surfactant additives are not incorporated, being replaced by the use of polar organic solvents of the present invention.

The pronounced effects when combining 1-triacontanol with other plant growth substances are shown in Table 3. Auxins, such as IAA, are found to counteract the effects of 1-triacontanol on plant growth, and other plant growth substances are shown to significantly alter the effect. In all cases, 1-triacontanol is found to promote the effects on plant growth of the plant growth substances, measured in terms of dry weight increases, except in the case of auxins, such as IAA.

The addition of metal ions of the invention having a valence of +2 or more shows an unexpected synergistic effect in increasing plant growth, as shown in Table 4. Furthermore, a number of metal ions are shown to cause this synergistic effect, many of which are not membrane-destabilizing members of the Hofmeister Series (Tables 4 and 5). Calcium, however, is the preferred metal ion of the invention, not due solely to its high degree of enhancement of 1-triacontanol-stimulated growth, but also to its high natural abundance, low cost, and exemption from tolerances by the U.S. Environmental Protection Agency. Other metal ions, particularly $Pb^{+2}$ and $Sr^{+2}$, or other metal ions, show an even higher degree of activity than calcium when combined with 1-triacontanol in the formulations of the invention, and while the use of these metal ions may not be advisable on plant life used for food purposes without determination of residues, they are useful in promoting the growth of other plant life, such as trees, flowers, ornamental plants, and the like, or other use described in the foregoing description of the invention.

In preliminary field trials during the 1980 growing season, the formulations of the invention were found to show increases in crop yields that were superior to those found using the prior art formulation, as shown in Table 6. In fact, two out of three crops tested showed decreases in crop yield when treated with the formulation of Ries, et al., U.S. Pat. No. 4,150,970. The improvement in formulation, therefore, is attributed to the use of the polar organic solvent, which is surfactant-free when diluted to the final formulation. The use of the surfactant in the prior art formulation, which uses a nonpolar solvent, furthermore, effectively complexes calcium ions or other polyvalent ions, and this may account for the seemingly toxic effect when the surfactant is utilized in formulations containing 1-triacontanol in many cases.

Increases in crop yields of three sweet corn cultivars, shown in Table 7, are shown to be both consistent and considerably greater than the increases observed without the addition of metal ions, thus demonstrating the practical utility of the formulations of the present invention under field conditions in two consecutive growing seasons.

Figure 2:
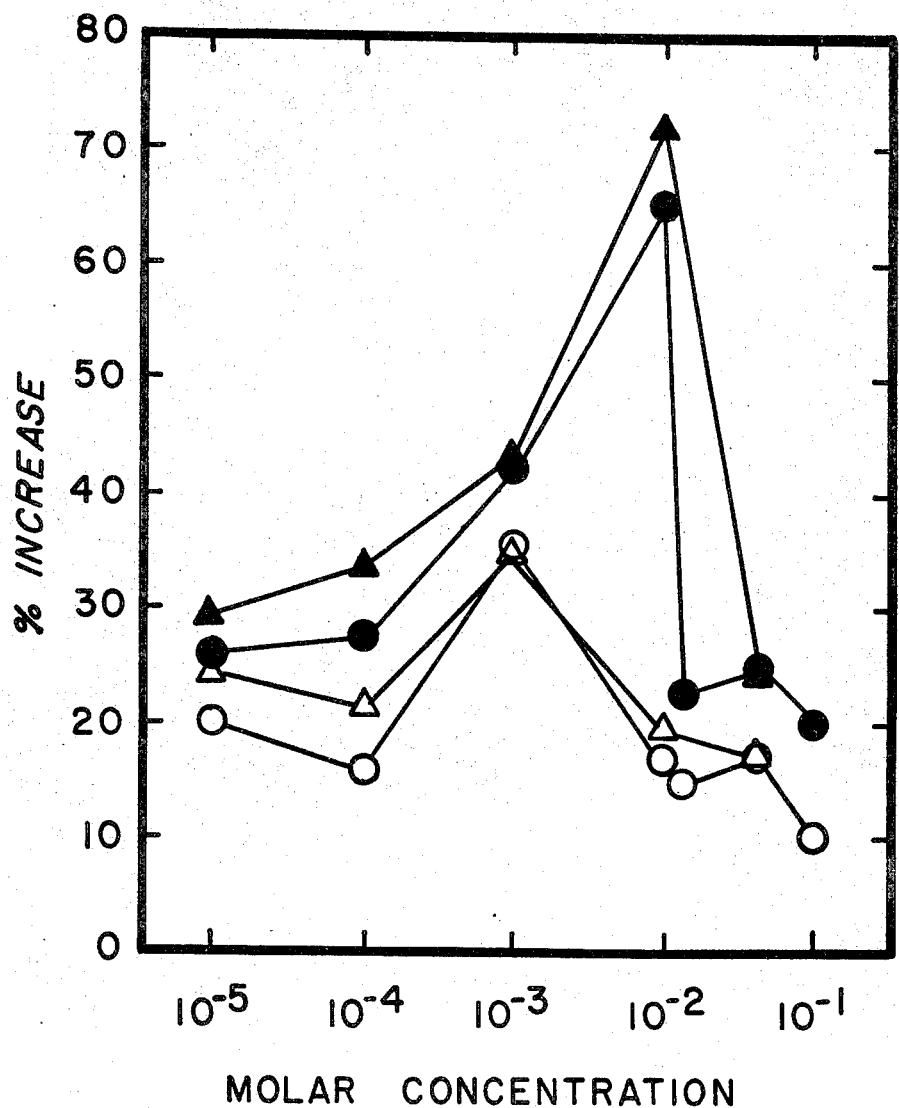
FIG. 2 is a graph showing the relationship between the concentration of $CaCl_2$ and $LaCl_3$ and the increases in dry weight and water uptake observed with sweet corn using surfactant-free formulations of 1-triacontanol containing 0.1 mg/liter of 1-triacontanol.

When the concentrations of the metal ions of the present invention are altered, the response of seedlings to 1-triacontanol is also altered. Thus, field corn seedlings have more narrow optimal range of concentrations at which a response is noted (Table 8) compared to sweet corn seedlings. FIG. 2 illustrates the effect of changing $Ca^{+2}$ and $La^{+3}$ concentrations on dry weight and water uptake increases over controls, and shows that, while a broad range of metal ion concentrations is effective, an optimum concentration of 10 mM is apparent. It is also important to note that concentrations in excess of the optimum reverse the synergistic effect, and therefore, when considering that hard water or well water used for spraying may contain amounts of metal ions, a safety margin produced by using a metal ion concentration somewhat lower than the optimum concentration may be advisable (e.g., using a metal ion concentration of 9 mM instead of 10 mM in the case of sweet corn).

Table 9 shows the changes in geometry of sweet corn seedlings sprayed with 1-triacontanol formulations containing $Ca^{+2}$, and the results therein are not to be considered as a measure of plant growth, which would be more accurately indicated by changes in the weight of the seedlings, especially dry weight changes. The results indicate that substantial increases are manifested in stalk thickness rather than height when data in the foregoing Tables are considered.

Table 10 clearly illustrates the synergistic effect of free metal ions having a valence of +2 or more (in this case $Ca^{+2}$) as opposed to complexed metal ions. The metal proteinate, described in the prior art by Ashmead in U.S. Pat. Nos. 4,169,716 and 4,169,717, is shown to be ineffective when combined with 1-triacontanol in the formulations described in the present invention. Furthermore, close inspection of the prior art references by Ashmead show that the synergistic effects of the metal proteinates when combined with other plant growth substances and with 1-triacontanol (U.S. Pat. No. 4,169,716) are clearly due primarily to said metal proteinates, and are attributed more to the presence of plant growth substances than 1-triacontanol. Calculation of actual increases from the data therein described shows that the enhancement of the effects by 1-triacontanol are only on the order of one to four percent. Also, as noted above, complexation of free metal ions by the formulation of Ries, et al., is detrimental to the effects of the formulations of the present invention, thereby confirming that only free metal ions and not complexed ions are effective in the formulations of the present invention.

Many other crops and other plant life show increases in growth which are not observed in the prior art. Table 12 shows the increases in dry weight and water uptake found when tomato seedlings are treated with the formulations of the instant invention. Treatment of the seedlings with the formulation of Ries, et al., again, show no effect on the seedlings, even when $CaCl_2$ is added to the formulation. The data also indicate that a metal ion concentration of about 5 mM or more is required for activity when the formulations of the present invention are employed. Other crops which are positively affected include sugar cane, beets, sugar beets, canteloupes, strawberries, potatoes, and the like. Crop yield data for two consecutive years have, furthermore, indicated that the increase found in the greenhouse trials indeed correlates well with the increases in actual crop yield found in field trials (Table 12). The patterns observed with respect to crop yield increases found per unit time with both tomatoes and beans are shown graphically in FIGS. 3 and 4, with the yield for tomatoes in the 1981 growing season becoming increasingly greater over controls as the growing season progressed.

The increase in growth, as measured in terms of dry weight, found when peas were sprayed with the formulations of the invention are shown in Table 13, with comparative field test data shown in Table 14. Peas, apparently, appear to be highly dependent upon a relatively high calcium concentration in the 1-triacontanol formulations to produce significant increases in growth over control plants. Again, the increases in dry weight observed in the greenhouse trials correlate with the increase in crop yield in the field, and this increase may be as much as twice that increase in dry weight observed under greenhouse-controlled environments.

Other crops show large increases in dry weight using the formulations of the present invention containing metal ions, such as watermelons (Table 15), wheat (Table 17), soybeans (Table 18), carrots (Table 21), and the like. The increases found in dry weight become manifest in crop yield increases, and in many cases, these increases are found to exceed the dry weight increases found in the greenhouse-controlled environment (Tables 16, 19, 20, 22, 23) or are found highly significant otherwise.

Effects have also been noted on ornamentals such as orchids, and the like, and tree seedlings sprayed with the formulations of the present invention show a marked increase in the number of lateral buds, which results in thicker stem diameter and a much larger number of resulting branches. Red maple trees show an increase in height over one year amounting to up to about 50%, and pine trees branch laterally rather than longitudinally over control plants. Other ornamental and tree seedlings may be expected to respond similarly to the formulations of the present invention, as well as other plant life.

It has further been observed by the present inventor that formulations of 1-triacontanol containing metal ions having a valence of +2 or more counteract the effects of herbicidal agents. For example, auxins and antiauxins, such as chlorophenoxyacetic acids and the like, are found to stimulate growth when applied to dicots when the formulations of the invention are applied as described in the foregoing description of the invention. Furthermore, the formulations may be applied before or after application of herbicidal agents, and may be of practical utility in protecting certain plant life from the subsequent application of herbicides which would otherwise act on said plant life, along with other uses. In this respect, larger amounts of 1-triacontanol may be used amounting up to 100 g. per liter in concentration, with an appropriate amount of metal ions in the solution or suspension. Other inert materials widely known in the art which affect the adhesion of the solution or suspension to said plant life are very useful, and prevent the loss of the formulation from the leaves of the plant life due to rainfall or other occurrence.

An important result from spraying the formulations of the present invention on plant life as described in the foregoing description is the effect on subsequent generations of plant life. It has been found, for the first time, that the seed obtained from plants which have been sprayed are larger in size compared to the control seed thus obtained, and that this increase is substantial (see Table 24). Upon planting the larger seed, an increase in the size of plants is apparent without spraying, and this increase is of approximately the same magnitude as if the control seeds were actually sprayed with the formulations of the present invention. Upon subsequent application of the formulations, an additional increase is observed, thereby producing an additive effect from one generation to another (Table 25). This effect may be expected to have a substantial impact on the improvement of world food shortage and fermented and other plant-derived fuel production at much reduced cost due to the additive amount of plant material used for such purpose obtained through subsequent generations.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A plant growth stimulator formulation, comprising:
    an effective plant growth-stimulating amount of 1-triacontanol;
    a polar organic solvent which is soluble in water, and in which 1-triacontanol is soluble;
    metal ions having a valence of +2 to +5, said metal ions being present in an amount effective to increase the plant growth-stimulating effects of said formulation; and
    water.

2. The formulation according to claim 1, wherein said metal ions are selected from the group consisting of $Ca^{+2}$, $La^{+3}$, $Sr^{+2}$, $Ba^{+2}$, $Cd^{+2}$, $Pb^{+2}$, $Zn^{+2}$, $Mn^{+2}$, $Mg^{+2}$, and $Ce^{+4}$.

3. The formulation according to claim 2, wherein the concentration of said metal ions is about $10^{-1}$ molar to about $10^{-5}$ molar.

4. The formulation according to claim 2, wherein the concentration of said metal ions is about $10^{-1}$ molar to about $10^{-3}$ molar.

5. The formulation according to claim 2, wherein said polar organic solvent is selected from the group consisting of alcohols, ketones, water-soluble ethers, glycols and organic carboxylic acids.

6. The formulation according to claim 2, wherein said polar organic solvent is selected from the group consisting of acetone, methyl ethyl ketone, methanol, ethanol, isopropanol, diethyleneglycol, n-butanol, dioxane, and acetic acid.

7. The formulation according to claim 6, wherein said polar organic solvent is a ketone.

8. The formulation according to claim 7, wherein said ketone is acetone.

9. The formulation according to claim 3, wherein said metal ion is $Ca^{+2}$.

10. The formulation according to claim 3, wherein said metal ion is $La^{+3}$.

11. The formulation according to claim 2, wherein said metal ion is selected from the group comprising $Zn^{+2}$, $Pb^{+2}$, $Sr^{+2}$, and $Ba^{+2}$.

12. The formulation according to claim 2, wherein said metal ion is $Mg^{+2}$.

13. The formulation according to claim 2, wherein the pH of said formulation is 7 or greater.

14. A method for stimulating plant growth which comprises applying an effective plant growth-stimulating amount of the formulation according to claim 1, to the area where plants are growing.

15. A method for stimulating plant growth which comprises applying an effective plant growth-stimulating amount of the formulation according to claim 2, to the area where plants are growing.

16. A method for stimulating plant growth which comprises applying an effective plant growth-stimulating amount of the formulation according to claim 9, to the area where plants are growing.

17. A method for stimulating plant growth which comprises applying an effective plant growth-stimulating amount of the formulation according to claim 10, to the area where plants are growing.

18. A method for stimulating plant growth which comprises applying an effective plant growth-stimulating amount of the formulation according to claim 11, to the area where plants are growing.

19. A method for stimulating plant growth which comprises applying an effective plant growth-stimulating amount of the formulation according to claim 12, to the area where plants are growing.

20. A method according to claim 15, wherein the formulation is applied to the leaves of plants by spraying.

21. A method according to claim 20, wherein the formulation is sprayed onto the leaves of growing plants when the plants have two to six leaves or sets of leaves.

22. A method according to claim 20, wherein the concentration of said metal ions is about $10^{-1}$ to $10^{-4}$ molar.

23. A method according to claim 20, wherein the concentration of said metal ions is about $10^{-1}$ to $10^{-3}$ molar.

24. A method according to claim 20, wherein the 1-triacontanol is sprayed in an amount of between 5 and 20 mg per acre.

25. A plant growth stimulator formulation consisting essentially of:
   an effective plant growth-stimulating amount of 1-triacontanol;
   a polar organic solvent which is soluble in water and in which 1-triacontanol is soluble, selected from the group consisting of alcohols, ketones, water-soluble ethers, glycols, sulfoxides, and organic carboxylic acids;
   metal ions having a valence of +2 or +3 in a concentration of between about 1 molar to about $10^{-5}$ molar and in an amount effective to increase the plant growth stimulating effects of said formulation; and
   water, wherein the ratio in parts by volume of the organic solvent to water is from 1:1 to 1:10,000.

26. The formulation according to claim 25, wherein the concentration of said metal ions is about $10^{-1}$ to about $10^{-3}$ molar.

27. The formulation according to claim 25, wherein said formulation contains an effective amount of $Ca^{+2}$ ions.

28. A method for stimulating plant growth comprising:
   applying an effective plant growth stimulating amount of triacontanol and an effective amount of metal ions having a valence of +2 or +3 in a concentration of 1 molar to $10^{-5}$ molar in an aqueous solution to the leaves of growing plants.

29. A method for stimulating plant growth which comprises applying an effective plant growth-stimulating amount of the formulation according to claim 27, to the area where plants are growing.

30. A method according to claim 20, wherein said plants are selected from the group consisting of corn, beans, cucumbers and tomatoes.

* * * * *